United States Patent [19]

Schappell

[11] 3,956,398

[45] May 11, 1976

[54] BIS-MONOPEROXYACETALS AND -KETALS

[75] Inventor: Frederick G. Schappell, Newark, Del.

[73] Assignee: Hercules Incorporated, Wilmington, Del.

[22] Filed: May 16, 1975

[21] Appl. No.: 578,221

[52] U.S. Cl. ................... 260/610 R; 260/79.5 R; 526/13; 526/14; 526/18; 526/20; 526/23; 526/55; 526/279; 526/295; 526/332; 526/339; 526/342
[51] Int. Cl.² ................................ C07C 179/06
[58] Field of Search .......... 260/610 R, 610 B, 80.3, 260/80.78, 94.9 R

[56] References Cited
UNITED STATES PATENTS

| | | |
|---|---|---|
| 3,030,386 | 4/1962 | Weissermel et al. ............ 260/610 R |
| 3,069,474 | 12/1962 | Rieche et al. .................. 260/610 R |
| 3,468,962 | 9/1969 | Ballini et al. .................. 260/610 R |

*Primary Examiner*—Bernard Helfin
*Assistant Examiner*—W. B. Lone
*Attorney, Agent, or Firm*—Charles L. Board

[57] ABSTRACT

Bis-monoperoxyacetals and bis-monoperoxyketals having the formula

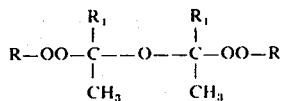

wherein R is selected from the group consisting of $C_4$–$C_{12}$ tertiary alkyl and $C_9$–$C_{12}$ tertiary aralkyl and $R_1$ is selected from the group consisting of hydrogen and $C_1$–$C_{12}$ alkyl, are effective crosslinking agents for polymers at relatively low cure temperatures.

6 Claims, No Drawings

BIS-MONOPEROXYACETALS AND -KETALS

This invention relates to novel bis-peroxyacetals and bis-peroxyketals and to their use as crosslinking agents for polymers such as polyethylene and the like.

In accordance with this invention it has been discovered that bis-monoperoxyacetals and bis-monoperoxyketals having the formula

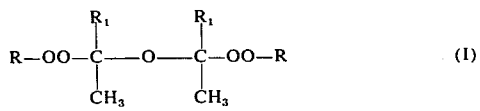

are effective crosslinking agents for polymers such as polyethylene at relatively low cure temperatures. Further, they are not significantly decomposed at temperatures used in preparing blends thereof with polymers prior to effecting crosslinking. In formula (I) R is selected from the group consisting of $C_4$–$C_{12}$ tertiary alkyl and $C_9$–$C_{12}$ tertiary aralkyl. $R_1$ is selected from the group consisting of hydrogen and $C_1$–$C_{12}$ alkyl. Examples of $C_4$–$C_{12}$ tertiary alkyl are t-butyl, t-amyl, t-octyl and t-dodecyl. Examples of tertiary aralkyl are cumyl ($\alpha,\alpha$-dimethylbenzyl); $\alpha,\alpha$-diethylbenzyl; and $\alpha$-methyl-$\alpha$-ethylbenzyl. Examples of $C_1$–$C_{12}$ alkyl are methyl, ethyl, propyl, isopropyl, butyl, isobutyl, tert-butyl, octyl, t-octyl, and dodecyl.

The bis-monoperoxyacetals and bis-monoperoxyketals of this invention are prepared by the addition reaction of a divinyl ether having the formula

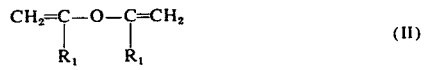

with a hydroperoxide of the formula R-OOH (III) wherein R and $R_1$ are as defined above. The addition reaction is catalyzed by an acid-acting catalyst.

Examples of divinyl ethers that can be used in the preparation of the bis-monoperoxyacetals and -ketals of this invention are divinyl ether, diisopropenyl ether, and diisobutenl-yl ether.

Examples of hydroperoxides that can be used are t-butyl hydroperoxide, t-amyl hydroperoxide, t-octyl hydroperoxide and cumene hydroperoxide.

Reaction of the divinyl ether with the hydroperoxide is carried out in liquid medium that is inert to the reactants and to the reaction product and which has a relatively low boiling point of from about 30°C. to 100°C. Illustrative liquid media are low boiling hydrocarbons, such, for example, as hexane and petroleum ether.

The addition reaction is catalyzed by any of the well known, acid-acting catalysts, including Friedel-Crafts type catalysts, mineral acid catalysts, organic sulfonic acids, and the like. Aromatic sulfonic acids such, for example, as p-toluene sulfonic acid are preferred. Reaction is conducted at temperatures from about 15°C. to about 60°C. and preferably from about 20°C. to about 40°C.

The following examples are illustrative of the invention. In the examples all parts and percentages are by weight unless otherwise specified.

EXAMPLE 1

A solution of 50.0 parts t-butyl hydroperoxide, and 198 parts petroleum ether (solvent) is prepared by mixing the reagents at 22°–25°C. The solution is azeotroped free of water by heating at reflux under atmospheric pressure for about one hour. After drying 0.66 part p-toluene sulfonic acid monohydrate is added. About 17.5 parts divinyl ether dissolved in 33 parts petroleum ether is added dropwise to the solution at a rate such that the temperature of the resulting reaction mass is maintained at about 22°–43°C. in a water bath. After about 2.75 hours the reaction mass is washed twice with 125 parts of 20% NaOH and then with 500 parts of water. The solvent is removed by evaporation under reduced pressure. The product is then dried over sodium sulfate. 52.6 Parts of a liquid product is obtained. Iodometric peroxide analysis and infrared spectroscopic analysis indicate that the product comprises 99.5% of the compound $\alpha,\alpha$-bis(t-butylperoxy)diethyl ether which has the formula

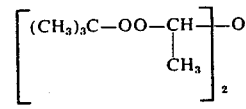

EXAMPLE 2

A solution of 1.4 parts divinyl ether, 0.05 part p-toluene sulfonic acid monohydrate and 16.5 parts petroleum ether (solvent) is prepared by mixing the ingredients. About 9.44 parts t-octylhydroperoxide (62% in hexane) diluted with 16.5 parts petroleum ether is added dropwise to the solution at a rate so that the temperature of the resulting reaction mass is maintained at about 25°–44°C. in a water bath. The reaction is continued for about 72 hours. The reaction mass is washed with 50 parts of 20% NaOH and then three times with 50 parts of water. The solvent is removed by evaporation under reduced pressure. The product is dried over sodium sulfate. 6.2 Parts of a liquid product is obtained. The product is shown by iodometric peroxide analysis and infrared spectroscope analysis to contain 67.0–77.1% of the compound $\alpha,\alpha'$-bis(2,4,4-trimethylpentyl-2-peroxy)diethyl ether which has the formula

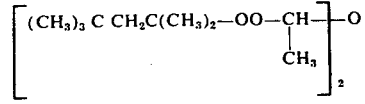

EXAMPLE 3

A solution of 134.3 parts t-amyl hydroperoxide in hexane, 0.2 part p-toluene sulfonic acid, is prepared by mixing the ingredients at 19°–24°C. for about five minutes. About 5.14 parts divinyl ether dissolved in 12.2 parts hexane is added dropwise at a rate such that the temperature of the resulting mass is maintained at 19°–51°C. The reaction is continued for about three hours. The reaction mass is washed twice with 125 parts of 5% and then three times with 50 parts of water. 27.4 Parts of a liquid product is obtained. The product is shown by iodometric peroxide analysis and infrared spectroscopic analysis to contain 66.5% of the compound α,α'-bis(t-amylperoxy)diethyl ether which has the formula

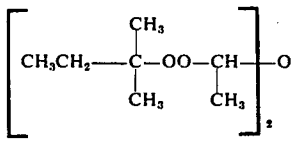

EXAMPLE 4

A solution of 14.0 parts divinyl ether, 23.2 parts cumene hydroperoxide and 198 parts petroleum ether (solvent) is prepared. About 0.2 part of the catalyst p-toluene sulfonic acid monohydrate is added to the solution. The reaction is continued for 5.33 hours at a temperature in the range of 15°–53°C. The resulting solution is washed twice with 125 parts of 5% NaOH and then three times with 50 parts of water. The solvent is removed by evaporation under reduced pressure and the product is dried over sodium sulfate. 24.7 Parts of a liquid product is obtained. The product is shown by iodometric analysis and infrared spectroscopic analysis to contain 72.9% of the compound α,α'-bis(cumylperoxy)diethyl ether which has the formula

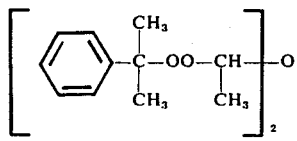

EXAMPLE 5

A solution of 25.0 parts t-butyl hydroperoxide, in 100 parts petroleum ether (solvent) is prepared by mixing the reagents at 23°–34°C. The solution is azeotroped free of water by heating at reflux under atmospheric pressure for about one hour. After drying, 0.5 part p-toluene sulfonic acid monohydrate is added. About 9.02 parts diisopropenyl ether is added dropwise to the solution of the hydroperoxide and catalyst at a rate such that the temperature of the reaction mass is maintained at 26°–33°C. The reaction is continued for 2.83 hours. The resulting solution is then washed with 125 parts of 5% NaOH and three times with 50 parts of water. The solvent is removed by evaporation under reduced pressure and the product is dried over sodium sulfate. 20.6 Parts of a liquid product is obtained. The product is shown by iodometric peroxide analysis and infrared spectroscopic analysis to be the compound having the formula

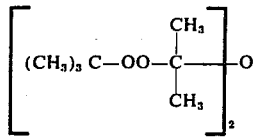

EXAMPLE 6

The peroxides prepared in Examples 1-5 are evaluated as crosslinking agents in ethylene-propylene-hexadiene terpolymer rubber. In each case, the peroxide is added to a composition containing 100 parts of ethylene-propylene-hexadiene terpolymer ("Nordel 1040"), 50 parts of carbon black (HAF Black N-330), 5 parts of zinc oxide, 0.5 parts of antioxidant (AgeRite Resin D, R. T. Vanderbilt Co., trademark for polymerized trimethyl dihydroquinoline) and clay (Burgess KE clay) in an amount equal to the amount of peroxide.

Curing half-lives and relative efficiencies of the peroxides are determined using a Monsanto Oscillating Disk Rheometer. This instrument measures viscosity increase with time at constant cure temperature of the polymer-peroxide composition. The viscosity increases as the peroxide decomposes and crosslinks the polymer. The thermal stability, or curing half-life, is determined by the rate at which the viscosity increases, and thus is a measure of the rate of decomposition of the peroxide. The curing efficiency of a given peroxide relative to an equivalent amount of dicumyl peroxide, a known curing agent, is determined from the magnitude of the viscosity change. Mooney scorch values are obtained using a shearing disk viscometer according to the procedure of ASTM D1646. The Mooney scorch value is the number of minutes required for a given viscosity increase to occur in the polymer-crosslinker composition at compounding temperatures (250°F.). The results are shown in Table I.

Table 1

| Peroxide | Purity (%) | Amount of Peroxide Used (parts) | Curing Half-Life (320°F.) (Min.) | Curing Efficiency* (% vs. Dicumyl Peroxide) | Mooney Scorch at 250°F. for 3 or 5 Point Rise in Viscosity (Min.) | |
|---|---|---|---|---|---|---|
| | | | | | 3 | 5 |
| Example 1 | 99 | 6.4 | 2.1** | 21 | | |
| | 99 | 1.26 | 4.1 | | | |
| | 92 | 4.2 | 1.4** | 23 | 13 | 21 |
| Example 2 | 67–77 | 2.70 | 1.6 | 34 | | |
| Example 3 | 66 | 4.20 | 1.3** | 12 | 9 | 15 |
| Example 5 | 109*** | 1.39 | 3.7 | 28.7 | 20 | 57 |
| Dicumyl Peroxide | 98.5 | 2.74 | 7.7 | 100 | 30 | >60 |

*Efficiency per peroxy bond
**330°F. half-life
***Impurities or secondary reactions gave apparent purity of 109%.

The short curing half-life of each of the peroxides of this invention at 320°F. indicates high rate of decomposition and high crosslinking reactively at this temperature.

Polymers which can be cured by means of the bisperoxyacetals and bis-peroxyketals of this invention are natural rubber, styrene butadiene rubber, polybutadiene rubber, polyisoprene rubber, nitrile rubber, acrylonitrile-butadiene-styrene, chloroprene rubber, ethylene-propylene copolymer, ethylene-propylene terpolymer, chlorinated polyethylene, chlorosulfonated polyethylene, acrylic rubbers, silicone rubbers, polysulfide rubbers, polyethylene, polyesters and polyurethanes. Compounding of the polymer and peroxide crosslinking agent can be carried out by any of the milling or mixing processes well known in the art of polymer processing.

The amount of bis-peroxyacetal or bis-peroxyketal incorporated in the polymer to effect crosslinking is usually in the amount of about 0.1 to about 15 parts per hundred parts of polymer. The crosslinking or curing process is accomplished by heating at a temperature in the range of 300 to 350°F. for a time sufficient to effect the desired cure.

What I claim and desire to protect by Letters Patent is:

1. A compound having the general structural formula

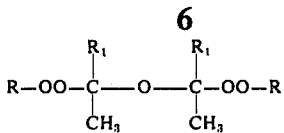

wherein R is selected from the group consisting of $C_4-C_{12}$ tertiary alkyl and $C_9-C_{12}$ tertiary alkylbenzyl. $R_1$ is selected from the group consisting of hydrogen and $C_1-C_{12}$ alkyl.

2. A compound of claim 1 in which each R is t-butyl and each $R_1$ is hydrogen.

3. A compound of claim 1 in which each R is cumyl and each $R_1$ is hydrogen.

4. A compound of claim 1 in which each R is t-octyl and each $R_1$ is hydrogen.

5. A compound of claim 1 in which each R is t-amyl and each $R_1$ is hydrogen.

6. A compound of claim 1 in which each R is t-butyl and each $R_1$ is methyl.

* * * * *